United States Patent [19]
Carr et al.

[11] Patent Number: 5,888,825
[45] Date of Patent: Mar. 30, 1999

[54] METHOD AND DEVICE FOR MONITORING CHANGES IN AN ARRAY OF SENSOR CONTAINING BOTTLES

[75] Inventors: Anthony Hugh Carr; Kenneth Cherry, both of Bedford; Simon Edward Jackson, Northampton, all of England

[73] Assignee: Oxoid Limited, Hampshire, England

[21] Appl. No.: 917,805

[22] PCT Filed: Feb. 9, 1994

[86] PCT No.: PCT/GB94/00253

§ 371 Date: Nov. 27, 1995

§ 102(e) Date: Nov. 27, 1995

[87] PCT Pub. No.: WO94/19698

PCT Pub. Date: Sep. 1, 1994

Related U.S. Application Data

[63] Continuation of Ser. No. 505,253, Oct. 27, 1995, abandoned.

[30] Foreign Application Priority Data

Feb. 17, 1993 [EP] European Pat. Off. ........... 93301166.0

[51] Int. Cl.⁶ ............................... C12Q 1/04; C12M 1/34
[52] U.S. Cl. ........................... 436/48; 435/34; 435/286.2; 435/287.3; 435/287.5; 435/288.7; 422/63; 422/82.05; 250/328; 436/43
[58] Field of Search ................................... 435/4, 29, 30, 435/33, 34, 39, 40, 286.2, 287.1, 287.3, 287.5, 288.7, 807, 808, 809; 422/63–66, 68.1, 82.05, 102; 436/43, 47, 48; 250/328; 356/246

[56] References Cited

U.S. PATENT DOCUMENTS

| | | | |
|---|---|---|---|
| 4,118,280 | 10/1978 | Charles et al. | 435/287.3 |
| 4,678,752 | 7/1987 | Thorne et al. | 435/287.3 |
| 4,692,308 | 9/1987 | Riley et al. | 422/65 |
| 4,952,498 | 8/1990 | Waters . | |
| 5,009,316 | 4/1991 | Klein | 206/443 |
| 5,281,394 | 1/1994 | Holub | 422/65 |
| 5,380,493 | 1/1995 | Chavez et al. | 422/99 |
| 5,397,709 | 3/1995 | Berndt | 435/288.7 |
| 5,516,692 | 5/1996 | Berndt | 435/286.7 |

FOREIGN PATENT DOCUMENTS

| | | |
|---|---|---|
| 252471 | 1/1986 | European Pat. Off. . |
| 2117309 | 11/1971 | Germany . |
| 2945524 | 5/1981 | Germany . |
| 93 3178 | 2/1993 | WIPO . |

*Primary Examiner*—William H. Beisner
*Attorney, Agent, or Firm*—Pillsbury Madison & Sutro, LLP

[57] ABSTRACT

Monitoring apparatus comprises a support device for receiving a plurality of items to be monitored in an array, each item having a unique machine-readable identifying reference associated therewith, the arrangement being such that the items are movable to different positions in the array; a sensor device for intermittently and repeatedly monitoring each item in the array to monitor changes in a variable associated with each item and to read the reference associated with each item; device for supplying data to the monitored variable and machine-readable reference of each item to a computer, wherein the computer relates the monitored variable to the reference to each item independently of the position of the item in the array.

9 Claims, 3 Drawing Sheets

140
METHOD AND DEVICE FOR MONITORING CHANGES IN AN ARRAY OF SENSOR CONTAINING BOTTLES

This application is a continuation of U.S. application Ser. No. 08/505,253, filed on Oct. 27, 1995, now abandoned, which was the National Stage of International Application No. PCT/GB94/00253, filed Feb. 9, 1994.

FIELD OF INVENTION

This invention concerns monitoring and relates to apparatus and methods for monitoring a variable associated with each of a plurality of items. The invention finds particular, but not exclusive, application in monitoring the growth of micro-organisms in blood culture bottles.

PRIOR ART

European Specification No. EP-A-252471 discloses a monitoring arrangement in which test pack trays are removably located in test pack drawers in a housing. The trays, but not the individual test packs, are referenced with a unique code which is detected by an X/Y scanner at the same time as the individual test packs are monitored. Data from the scanner is fed to a computer. The computer is thus able to relate the individual test pack signals to particular trays, but the location of any particular test pack to which particular data relates is unknown. This problem is overcome by means of a sorter controller, which maps a computer associated memory with the positions of individual test packs in each tray when the trays are loaded. The map thus requires to be updated if the test packs are re-arranged.

The requirement to provide a sorter controller which is required to map a memory associated computer is clearly disadvantageous and tends to inhibit full re-arrangement of the trays when the test packs are being examined.

The present invention aims to overcome this disadvantage.

SUMMARY OF THE INVENTION

In one aspect the present invention provides monitoring apparatus comprising a unit having one or more supports each for receiving a plurality of items in an array in which the items are re-locatable, sensor means for intermittently and repeatedly monitoring each item in the array to monitor changes in a variable associated therewith, and means for supplying data relating to the monitored variable to computer means, characterised in that each item has a unique machine-readable identifying reference associated therewith, which reference is read by the sensor means and supplied to the computer means, together with the data relating to the monitored variable, and in that the computer means is programmed to relate the monitored variable to the reference of each item independently of the location of the item in the array.

By having a unique machine-readable reference associated with each item which is read and by having data thereon supplied to the computer means together with data on the monitored variable, the computer is able to monitor data on the variable of a particular item regardless of the location of the item within the array and regardless of changes of location of items in the array. Monitoring is thus linked to the item independent of location in the array. This means that items can be moved within the array at will, eg. for "housekeeping" purposes, without affecting monitoring. There is further no need to allocate a particular location in the array to a particular item, with the risk of inadvertent substitutions. There is similarly no need to keep a location free for an item temporarily removed from the array, eg. for further investigation.

The items can be anything requiring repeated monitoring over an extended period. The invention finds particular application in monitoring micro-organism growth in liquid culture, eg. blood samples, in a gas-tight containers each incorporating a flexible diaphragm capable of moving in response to pressure changes within the container, by detecting displacement of the diaphragm, wherein the position or conformation of the diaphragm is repeatedly sensed using distance-measuring means such as a laser, eg. as disclosed in PCT/GB92/01327 (WO93/03178). In this case the items typically comprise blood culture bottles and the variable monitored is diaphragm position, which is indicative of internal pressure, which in turn is indicative of micro-organism growth. Other variables such as temperature, colour, electrical properties etc could alternatively be monitored.

The support conveniently comprises a generally stationary holder such as a drawer in a housing, with respect to which the sensor means moves to monitor the items in turn. Alternatively, the support can be movable for presenting items in the array in turn to generally stationary sensor means, eg. with the supports arranged as a carousel.

The machine-readable reference conveniently comprises a barcode. In this case the sensor means comprises a barcode reader.

The computer means will typically also control and coordinate relative movement of the support means and the sensor means in known manner for monitoring of the items.

There are circumstances in which it may be desirable for particular items in the array to be marked, eg. to signal an abnormality in the monitored variable detected by the computer means. In this case, the support means conveniently includes a plurality of indicator means each associated with a particular location in the array and each selectively activable, typically under control of the computer means, to provide a visual marker or flag linked to the item in the associated location in the array. In this case an item in a marked location in the array is effectively no longer movable within the array. The markers conveniently comprise lights, preferably LEDs.

In a preferred aspect, the invention thus provides monitoring apparatus comprising a unit for receiving one or more drawers each for receiving a plurality of items in an array in which the items are re-locatable, sensor means for intermittently and repeatedly monitoring each item in the array to monitor changes in a variable associated therewith, and means for supplying data relating to the monitored variable to commuter means, characterised in that a plurality of indicator means are provided, each associated with a particular location in the array and each selectively activatable; in that each item has a unique machine-readable identifying reference associated therewith, which reference is read by the sensor means and supplied to the computer means together with the data relating to the monitored variable; in that the computer means is programmed to relate the monitored variable to the reference of each item independent of the location of the item in the array; and in that the computer means also controls activation of the indicator means.

A respective indicator means, eg. LED, is preferably associated with each location in the array.

The invention also provides a method of monitoring a variable associated with each of a plurality of items, each item having a unique machine-readable identifying reference associated therewith, comprising locating the items in an array in a withdrawable drawer in a housing within which array the items can be relocated; intermittently and repeatedly monitoring each item in the array both to monitor changes in the variable and to read the associated reference; supplying data relating to the monitored variable and machine-readable reference of each item to computer means; and programming the computer means to relate the monitored variable to the reference of each item independent of the location of the item in the array.

In a further aspect the invention provides a method of monitoring a variable associated with each of a plurality of items, each item having a unique machine-readable identifying reference associated therewith, comprising locating the items in an array in a support in a housing, within which array the items can be re-located; intermittently and repeatedly monitoring each item in the array both to monitor changes in the variable and to read the associated reference; supplying data relating to the monitored variable and machine-readable reference of each item to computer means; programming the computer means to relate the monitored variable to the reference of each item independent of the location of the item in the array; and changing the location of one or more items in the array prior to further monitoring.

An embodiment of the invention involving monitoring of micro-organism growth in blood culture bottles will now be described, by way of illustration, with reference to the accompanying drawings, in which.

DETAILED DESCRIPTION OF THE DRAWINGS

The illustrated apparatus is generally as described in PCT/GB92/01327 (WO93/03178), and reference can be made to the specification of that application for a more detailed description and explanation.

Figure 1:
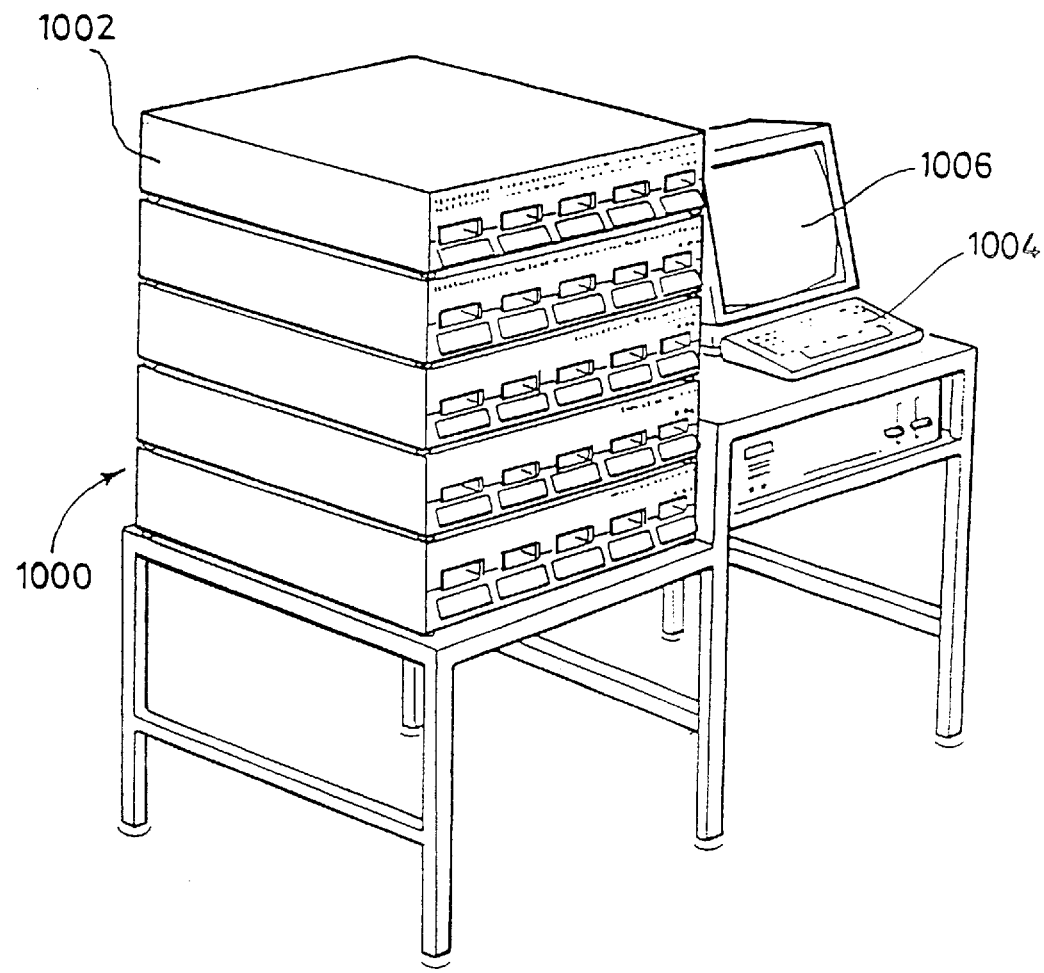
FIG. 1 is a diagrammatic perspective view of an automated culture unit comprising an embodiment of apparatus in accordance with the invention.

FIG. 1 shows a unit 1000 removable housing 5 similar drawers 1002 for receiving bottles, and also computer control means 1004 with an associated visual display unit 1006.

Figure 2:
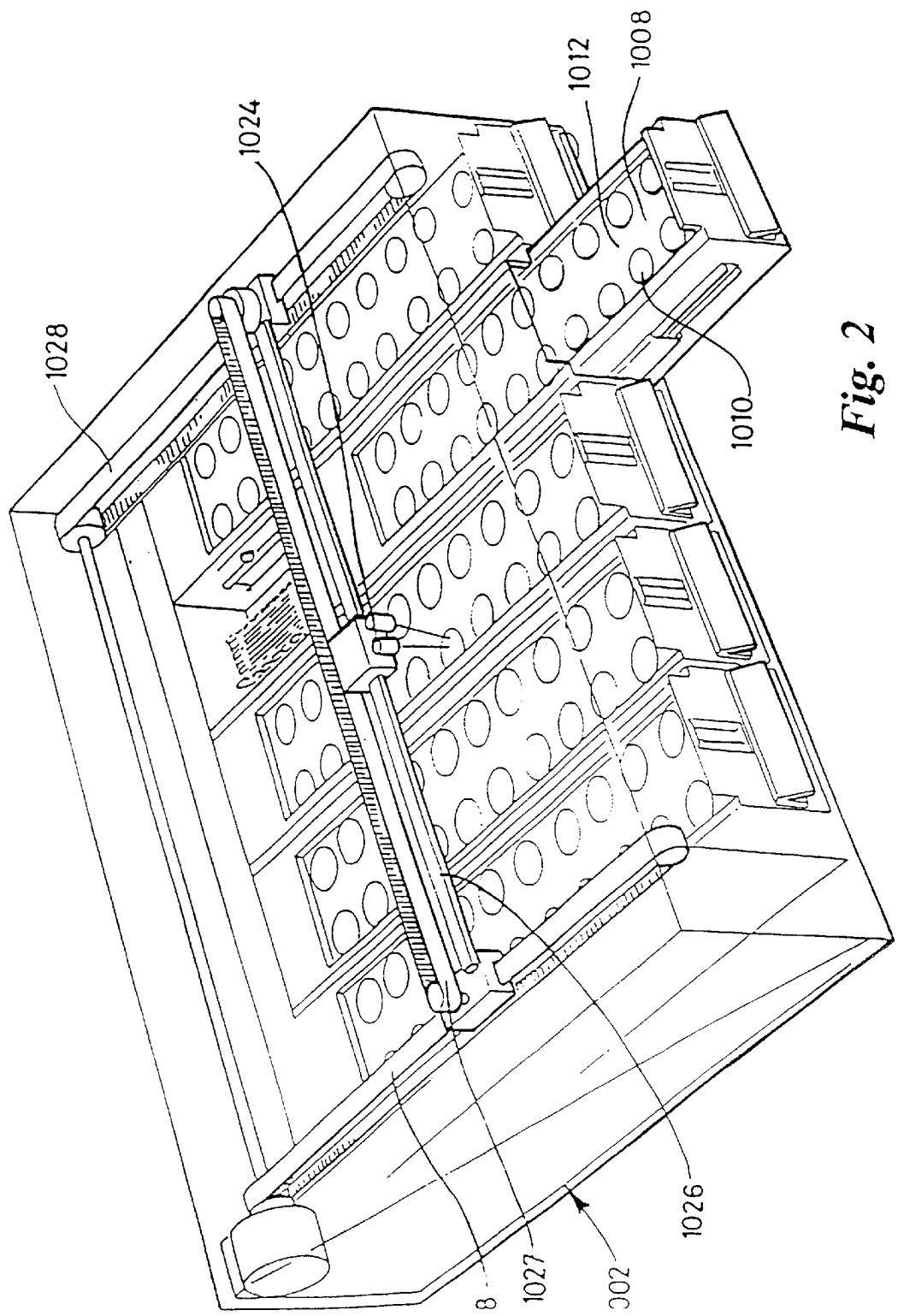
FIG. 2 is a perspective view of part of the unit of FIG. 1, shown to an enlarged scale.

As shown in FIG. 2 each drawer 1002 comprises 5 similar supports 1008, each slidably received therein and independently removable therefrom. Each support 1008 comprises two apertured aluminium blocks defining two side by side rows of 10 similar recesses 1010, each for receiving a respective sample bottle (FIG. 3), so that the bottle is fully received within the recess for good temperature regulation.

A respective LED 1012, only one of which is shown in FIG. 2 for clarity, is associated with each recess 1010.

Each drawer 1002 further comprises a laser 1024 (eg. a Matsushita LA40 laser) and barcode reader (not shown separately), possibly combined together in a purpose built unit, mounted for movement in two perpendicular directions (X and Y) on a generally conventional X-Y motion controller. The controller comprises a cross-rail 1026 on which laser 1024 and barcode reader are mounted for sliding movement in an X direction under the action of a stepper-motor driven belt drive 1027. The ends of rail 1026 are carried by stepper-motor driven belt drives 1028, for causing movement in a Y direction.

Figure 3:
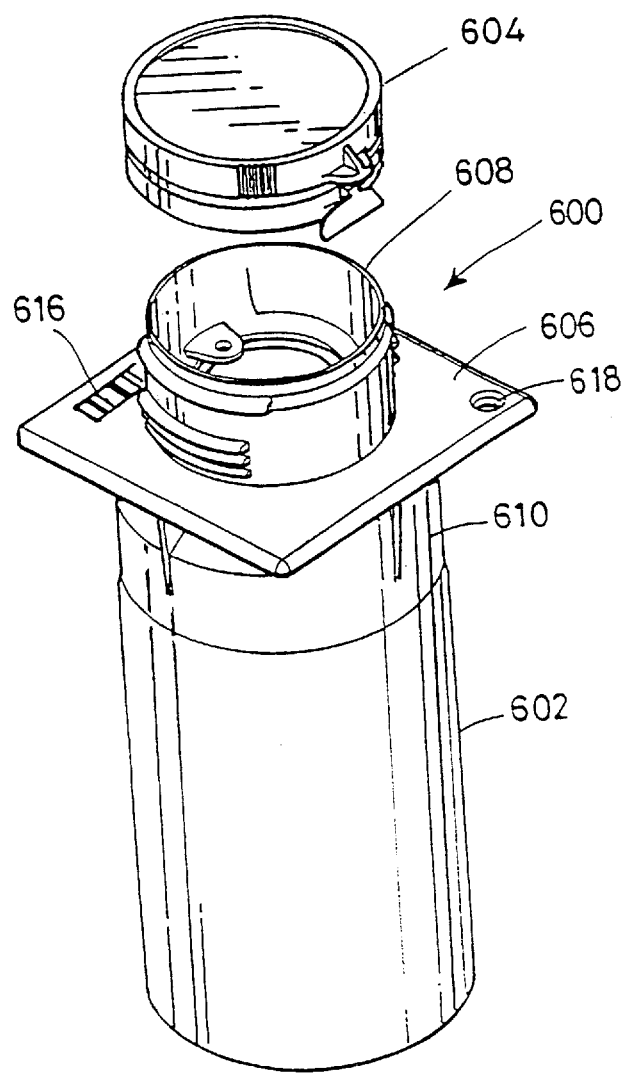
FIG. 3 is a perspective view of a culture bottle with overcap for use in the apparatus of FIGS. 1 and 2.

FIG. 3 illustrates a blood culture bottle 602 suitable for use with the apparatus of FIGS. 1 and 2. Bottle 602 incorporates a resilient flexible diaphragm or septum (not visible in FIG. 3) that deforms in response to changes in pressure within the bottle. The bottle typically contains liquid growth medium and a blood or other sample to be monitored for micro-organism content, as described in PCT/GB92/01327 (WO93/03178).

The bottle 602 is FIG. 3 is shown fitted with a plastics overcap (or overcover) 600 with a tamper-evident tear-off portion removed. The overcap is described in more detail in European Application No. 93301173.6 (PCT/GB94/00256, published as WO94/19452), overcap 600 has all round a generally square lateral projection 606 which is relatively thin, so that the body of the cap has cylindrical sections 608 and 610 respectively above and below the square projection. The lower cylindrical section 610 has internally a lip which snap-fits over the bottle seal (not shown).

The upper surface of the projection 606 is on one side marked with a barcode 616 for bottle identification purposes, and on the opposite side, adjacent one corner, has a port 618 at which, when the bottle is in use the apparatus of FIGS. 1 and 2, a respective LED 1012 uniquely associated with each recess 1010 can be viewed.

In use, bottles 602 containing samples to be monitored, each with a respective overcap 600 with a unique barcode 616 (including an individual number, plus batch code and expiry data), are loaded into the apparatus of FIGS. 1 and 2 by locating the bottles in vacant recesses 1010 and entering information regarding the bottles and their barcodes to computer control means 1004. Additional information regarding the bottles, eg. lab sample register number, lab barcode surname, ward etc may be entered into computer control means if required. The location of the bottles in the array is not important, and an vacant location can be used for any bottle.

Preferably, the barcode is applied in duplicate to a dual two section label, one section fixed to the overcap and one section left floating and detachable via perforations. The floating section can have a peel-off backing so that, after detachment, it can be used to label a record card or the like with the same bar code.

The unit 1000 is then operated, as described in PCT/GB92/01327 (WO93/013178), with suitable incubation conditions established therein and the scanner 1024 of each dragger in use being operated intermittently and repeatedly to scan each bottle in that drawer, reading the barcode (thus identifying the bottle, regardless of location) and measuring septum position for each bottle on each scan. Data concerning the barcode and septum position is fed to commuter control means 1004.

The apparatus senses any operator intervention and assumes removal or relocation of bottles: on the first subsequent scan the computer control means 1004 rationalises bottle identification data obtained from barcodes with coordinates. This feature allows periodic "housekeeping" to regroup bottles and reorganise contents of the apparatus. There may be a need to remove, sample and replace a bottle: again location within the array is not important because there is effectively random access. When a bottle is removed the computer control means can recognise and prompt if the bottle is not replaced somewhere within the apparatus within a reasonable time.

In this system, all data collected is linked to the bottle identification (obtained from the barcode), regardless of location in the array or indeed changes of location. There is no need to allocate locations (with the associated risk of inadvertent substitutions.). Similarly there is no need to keep a location open for a bottle under temporary investigation. The link between bottle identity and data is totally independent of the operator.

There are circumstances in which the operator does become involved and it is necessary to "flag" specific bottles. For this purpose the overcap 660 is linked to an individual LED 1012 by illuminating the particular LED at the location of the bottle, the LED being visible through port 618. In addition to any screen display on unit 1016 the operator has clear, local indication of the bottle(s) to be dealt with by virtue of illumination of the associated LED. The result of a blood culture test is either positive (indicated as soon as detected) or negative. In the latter case the computer can flag bottles for removal at the end of some predetermined period (eg. 7 days). In some situations the operator may need to locate specific bottles, in order to intervene with other types of investigation. For this type of interaction the system can operate a "find-a-bottle" routine to locate and highlight the target samples.

The three way link between bottle/cap (code and LED), associated data and the operator is simple and robust. Technicians find operation of the system very "natural", flexible and deceptively simple.

We claim:

1. Monitoring apparatus comprising a unit having at least one support, the at least one support carrying a plurality of items in an array, sensor means, means for reactively moving the at least one support and the sensor means to intermittently and repeatedly scan each item in the array to monitor changes in a variable associated therewith, and means for supplying data relating to the monitored variable to computer means, wherein each item has a unique machine-readable identifying reference thereon, which reference is read by the sensor means during scanning and supplied to the computer means together with the data relating to the monitored variable, the computer means is programmed to relate the monitored variable to the reference of each item independently of the location of the item in the array, and means are provided to enable the removal, relocation and addition of items in the array in the at least one support, the computer means also being programmed to cause a location and identifying reference scan to be performed immediately after a possible item removal, relocation or addition in the array and re-relate the monitored variables each to its corresponding reference.

2. Apparatus according to claim 1, wherein the items comprise gas-tight containers each incorporating a flexible diaphragm capable of moving in response to pressure changes within the container, and wherein the sensor means detects displacement of the diaphragms.

3. Apparatus according to claim 2, wherein the sensor means comprises a laser.

4. Apparatus according to claim 1, wherein the machine-readable reference comprises a barcode, and the sensor means includes a barcode reader.

5. Apparatus according to claim 1, wherein the or each support is a withdrawable drawer in a housing, and the sensor means is movable within the housing with respect to the drawer.

6. Monitoring apparatus comprising a unit having one or more drawers each carrying a plurality of items in an array, sensor means for intermittently and repeatedly monitoring each item in the array to monitor changes in a variable associated therewith, and means for supplying data relating to the monitored variable to computer means, a plurality of indicator means, each associated with a particular location in the array and each selectively activatable, wherein each item has a unique machine-readable identifying reference thereon, which reference is read by the sensor means and supplied to the computer means together with the data relating to the monitored variable; the computer means is programmed to relate the monitored variable to the reference of each item independently of the location of the item in the array; and the computer means also controls activation of the indicator means, and means are provided to enable the removal, relocation and addition of items in the array in the at least one support, the computer means also being programmed to cause a location and identifying reference scan to be performed immediately after a possible item removal, relocation or addition in the array and re-relate the monitored variables each to its corresponding reference.

7. Apparatus according to claim 6, wherein each indicator means comprises an LED.

8. A method of monitoring a variable associated with each of a plurality of items, each item having a unique machine-readable identifying reference thereon, comprising locating the items in an array in a withdrawable drawer in a housing within which array items can be withdrawn, relocated or added, intermittently and repeatedly monitoring each item in the array both to monitor changes in the variable and to read the associated reference; supply data relating to the monitored variable and machine-readable reference of each item to computer means; and programming the computer means firstly to relate the monitored variable to the reference of each item independent of the location of the item in the array, and secondly to cause a location and identifying reference scan to be performed immediately after a possible item removal, relocation or addition in the array and re-relate the monitored variables each to its corresponding reference.

9. A method of monitoring a variable associated with each of a plurality of items, each item having a unique machine-readable identifying reference associated therewith, comprising locating the items in an array in a support in a housing, within which array items can be withdrawn, relocated, or added; intermittently and repeatedly monitoring each item in the array both to monitor changes in the variable and to read the associated reference; supplying data relating to the monitored variable and machine-readable reference of each item to computer means; programming the computer means to relate the monitored variable to the reference of each item independent of the location of the item in the array; removing, changing the location of or adding one or more items in the array prior to further monitoring; and additionally programming the computer to cause a location and identifying reference scan to be performed immediately after a possible item removal, relocation or addition in the array and re-relate the monitored variables each to its corresponding reference.

\* \* \* \* \*